(12) United States Patent
Hwang et al.

(10) Patent No.: US 11,786,327 B2
(45) Date of Patent: Oct. 17, 2023

(54) TELE-OPERATED FORCEPS-DRIVER VARIABLE STIFFNESS MASTER DEVICE

(71) Applicant: KOREA INSTITUTE OF SCIENCE AND TECHNOLOGY, Seoul (KR)

(72) Inventors: Donghyun Hwang, Seoul (KR); Sungwoo Park, Seoul (KR); Namseon Jang, Seoul (KR); Yong Seok Ihn, Seoul (KR); Sungwook Yang, Seoul (KR); Jinwoo Jeong, Seoul (KR); Sehyuk Yim, Seoul (KR); Sang Rok Oh, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 555 days.

(21) Appl. No.: 17/029,286

(22) Filed: Sep. 23, 2020

(65) Prior Publication Data

US 2021/0244490 A1    Aug. 12, 2021

(30) Foreign Application Priority Data

Feb. 10, 2020    (KR) ........................ 10-2020-0015706

(51) Int. Cl.
*A61B 34/35* (2016.01)
*A61B 17/29* (2006.01)
(Continued)

(52) U.S. Cl.
CPC .............. *A61B 34/35* (2016.02); *A61B 17/29* (2013.01); *A61B 34/37* (2016.02); *A61B 34/74* (2016.02);
(Continued)

(58) Field of Classification Search
CPC ......... A61B 34/35; A61B 17/29; A61B 34/37; A61B 34/74; A61B 34/76;
(Continued)

(56) References Cited

U.S. PATENT DOCUMENTS

| 6,594,552 B1 | 7/2003 | Nowlin et al. |
| 2012/0071863 A1 | 3/2012 | Lee et al. |

(Continued)

FOREIGN PATENT DOCUMENTS

| EP | 3705043 A1 | 9/2020 |
| JP | H07184923 A | 7/1995 |

(Continued)

OTHER PUBLICATIONS

Sungwoo Park et al., "A Tele-Operated Microsurgical Forceps-Driver With a Variable Stiffness Haptic Feedback Master Device", IEEE Robotics and Automation Letters, Apr. 2020, pp. 1946-1953, vol. 5, No. 2.

*Primary Examiner* — Kelly J Bekker
*Assistant Examiner* — Mohammed S Adam
(74) *Attorney, Agent, or Firm* — Rabin & Berdo, P.C.

(57) ABSTRACT

Provided is a tele-operated forceps-driver variable stiffness master device including a master member to generate an input displacement signal generated by pressing with a user's finger, and a slave member to operate based on the input displacement signal, measure operation information, calculate a gripping force based on the operation information, and provide the master member with at least one of a stiffness change command signal or a force feedback based on the calculated gripping force.

7 Claims, 16 Drawing Sheets

(51) Int. Cl.
   *B25J 3/04*     (2006.01)
   *A61B 17/00*    (2006.01)
   *B25J 13/08*    (2006.01)
   *A61B 34/37*    (2016.01)
   *A61B 34/00*    (2016.01)
   *A61B 34/30*    (2016.01)

(52) U.S. Cl.
   CPC ............... *A61B 34/76* (2016.02); *B25J 3/04* (2013.01); *A61B 2017/00022* (2013.01); *A61B 2017/00367* (2013.01); *A61B 2017/00398* (2013.01); *A61B 2017/2912* (2013.01); *A61B 2034/306* (2016.02); *B25J 13/082* (2013.01)

(58) Field of Classification Search
   CPC ........... A61B 2017/00022; A61B 2017/00367; A61B 2017/00398; A61B 2017/2912; A61B 2034/306; A61B 2090/062; A61B 2090/064; A61B 2090/067; A61B 17/00234; A61B 2017/003; A61B 2017/2932; B25J 3/04; B25J 13/082
   See application file for complete search history.

(56) References Cited

U.S. PATENT DOCUMENTS

2019/0171290 A1    6/2019  Hwang et al.
2020/0289229 A1*   9/2020  Denlinger ................ A61B 1/04

FOREIGN PATENT DOCUMENTS

| JP | 2019118546 A  |   | 7/2019  |              |
|----|---------------|---|---------|--------------|
| JP | 2020005866 A  | * | 1/2020  | ... A61B 17/29 |
| JP | 2020005866 A  |   | 1/2020  |              |
| KR | 1020120030174 A |  | 3/2012  |              |
| KR | 101830389 B1  |   | 2/2018  |              |
| KR | 1948079 B1    | * | 5/2019  | ... G06F 3/011 |
| KR | 101948079 B1  |   | 5/2019  |              |
| KR | 1020200003653 A |  | 1/2020  |              |

* cited by examiner

TELE-OPERATED FORCEPS-DRIVER VARIABLE STIFFNESS MASTER DEVICE

CROSS-REFERENCE TO RELATED APPLICATION

This application claims priority to Korean Patent Application No. 10-2020-0015706, filed on Feb. 10, 2020, and all the benefits accruing therefrom under 35 U.S.C. § 119, the contents of which in its entirety are herein incorporated by reference.

BACKGROUND

1. Field

The present disclosure relates to a tele-operated forceps-driver variable stiffness master device, and more particularly, to a tele-operated forceps-driver variable stiffness master device capable of feeding back the sensation of a forceps driver being operated while controlling the forceps driver.

[Description of Government-Funded Research and Development]

This research is conducted by Korea Institute of Science and Technology, and funded by STEAM research (system integration and testing of bionic arm with biosignal based control function, No. 1711097690) of National Research Foundation of Korea, Ministry of Science and ICT, Republic of Korea.

2. Description of the Related Art

A surgical robot end effector for driving forceps is well known.

A forceps driver is a device in which two wheels positioned on top of linear sliders driven by an electric motor operate in the lengthwise direction of forceps, and grip of the forceps is enabled by the operation.

The forceps driver is difficult to achieve precise measurement and fine control of a gripping force applied to the tissue when gripping the tissue due to the absence of a gripping force measurement sensor.

A tele-manipulator is designed to manipulate a slave device using a button mounted in a pen of a master device or a separate pedal, but this method is difficult to manipulate the device intuitively.

Additionally, when remote surgery is performed using the tele-manipulator in reliance on visual feedback without haptic feedback, surgeons themselves cannot identify grasping manipulation and forces applied to the tissues.

SUMMARY

The present disclosure is directed to providing a tele-operated forceps-driver variable stiffness master device capable of feeding back the sensation of a forceps driver being operated while controlling the forceps driver.

The present disclosure is designed to solve the above-described problem, and a tele-operated forceps-driver variable stiffness master device of the present disclosure includes a master member to generate an input displacement signal generated by pressing with a user's finger, and a slave member to operate based on the input displacement signal, measure operation information, calculate a gripping force based on the operation information, and provide the master member with at least one of a stiffness change command signal or a force feedback based on the calculated gripping force.

According to an example related to the present disclosure, the master member may include a button that is pressed in one direction when the finger contacts the button, a deformable membrane connected to the button and extending in a direction perpendicular to the one direction so that the deformable membrane is deformed by the pressing of the finger, and a wire that is deformed in contraction when supplied with power to restore the deformable membrane to an original state.

The master member may further include a flange installed outside of the deformable membrane to support the deformable membrane, and a plurality of wire fixtures installed at each of the flange and the deformable membrane to fixedly install the wire.

Additionally, the master member may be symmetric with respect to a neutral base, and the master member may further include a displacement sensor installed on one surface of the deformable membrane disposed near the neutral base to sense displacement of the deformable membrane and generate the input displacement signal, and a magnet that is spaced apart from the displacement sensor and installed on one surface of a different deformable membrane with the neutral base interposed between.

The master member may further include a force sensor installed in the button to sense a force applied by the contact with the finger.

In an initial condition, when the button is pressed, the deformable membrane may be elastically deformed, displacement of the deformable membrane may be measured by the displacement sensor, and the slave member may operate by the displacement of the deformable membrane.

According to another example related to the present disclosure, the tele-operated forceps-driver variable stiffness master device of the present disclosure may further include a control unit to receive displacement or force information from the master member and control the gripping force of the slave member, and receive displacement or force information from the slave member and control target stiffness of the master member.

According to still another example related to the present disclosure, the slave member may include a gripper that is deformed to be open and closed, a body formed to receive the gripper, and an opening and closing member rotatably installed in the body to press or release two sides of the gripper.

Additionally, a rotational displacement sensor and a force sensing module may be installed in the body, wherein the rotational displacement sensor measures an extent of grasp of the gripper by measuring an amount of rotation of the opening and closing member, and the force sensing module is interposed between the opening and closing member and the gripper to measure the gripping force during the operation of the opening and closing member.

A motor may be installed in the body to generate a driving force, and a steel wire may be installed between the motor and the gripper to provide the driving force to allow the gripper to grasp.

DETAILED DESCRIPTION

Hereinafter, the disclosed embodiments will be described in detail with reference to the accompanying drawings, and identical or similar elements are given identical or similar reference signs and redundant descriptions are omitted herein. As used herein, the suffix "unit" is only given or used to ease the drafting of the specification, and does not have any meaning or role for identifying itself. Additionally, in describing the embodiments disclosed herein, when it is determined that a certain detailed description of relevant known technology may make the key subject matter of the disclosed embodiments ambiguous, the detailed description is omitted herein. Additionally, the accompanying drawings are provided for an easy understanding of the disclosed embodiments, and the technical spirit disclosed herein is not limited by the accompanying drawings, and it should be understood that the present disclosure covers all modifications, equivalents or substitutes falling in the spirit and technical scope of the present disclosure.

The terms "first", "second", and the like may be used to describe various elements, but the elements are not limited by the terms. These terms are used to distinguish one element from another.

It will be understood that when an element is referred to as being "connected to" another element, the element can be connected to the other element, but intervening elements may be present.

Unless the context clearly indicates otherwise, the singular forms include the plural forms as well.

It should be understood that the term "comprises" or "includes" when used in this specification, specifies the presence of stated features, integers, steps, operations, elements, components or groups thereof, but does not preclude the presence or addition of one or more other features, integers, steps, operations, elements, components, or groups thereof.

Figure 1:
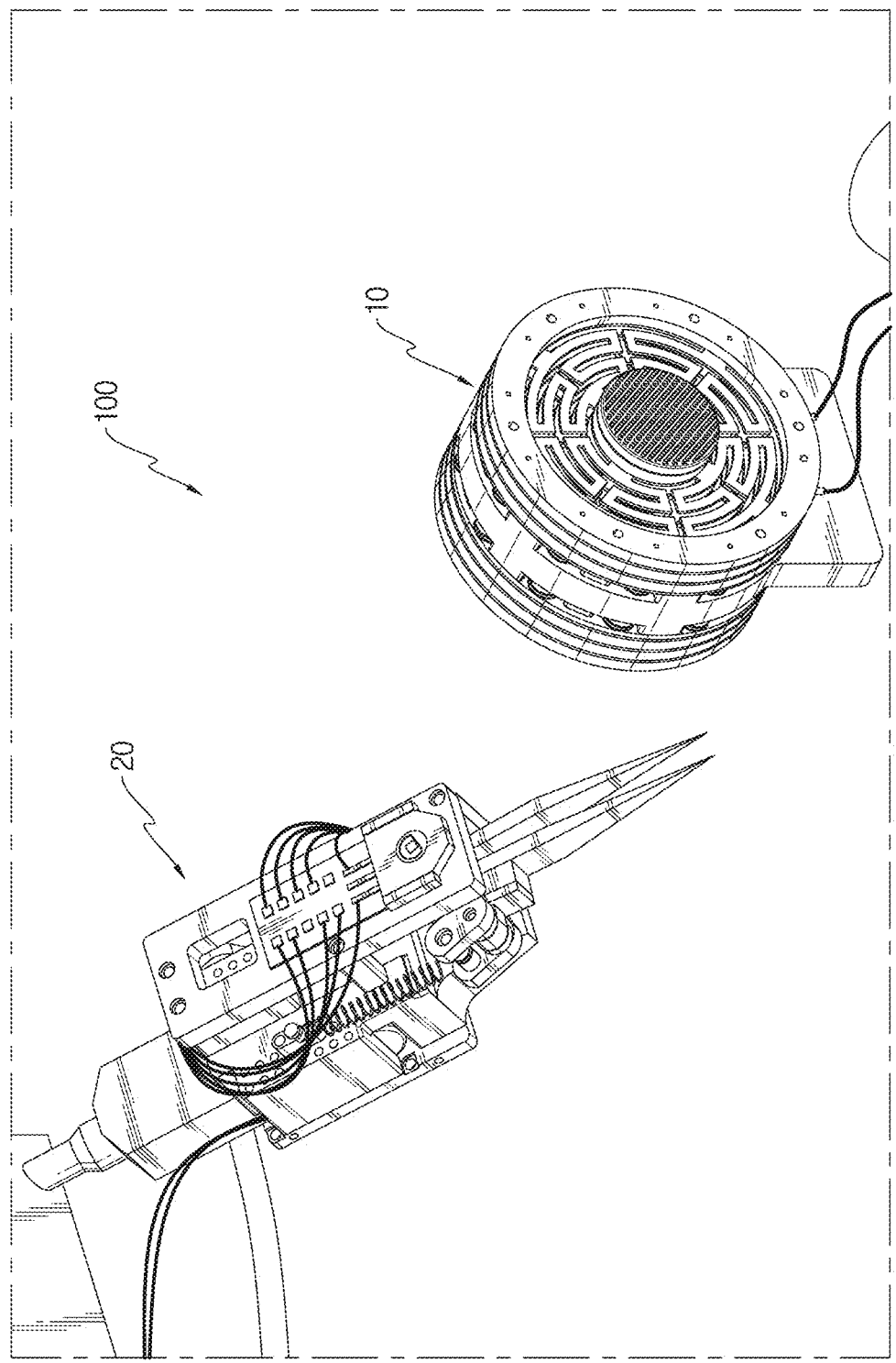
FIG. 1 is a perspective view showing a tele-operated forceps-driver variable stiffness master device of the present disclosure.
Figure 2A:
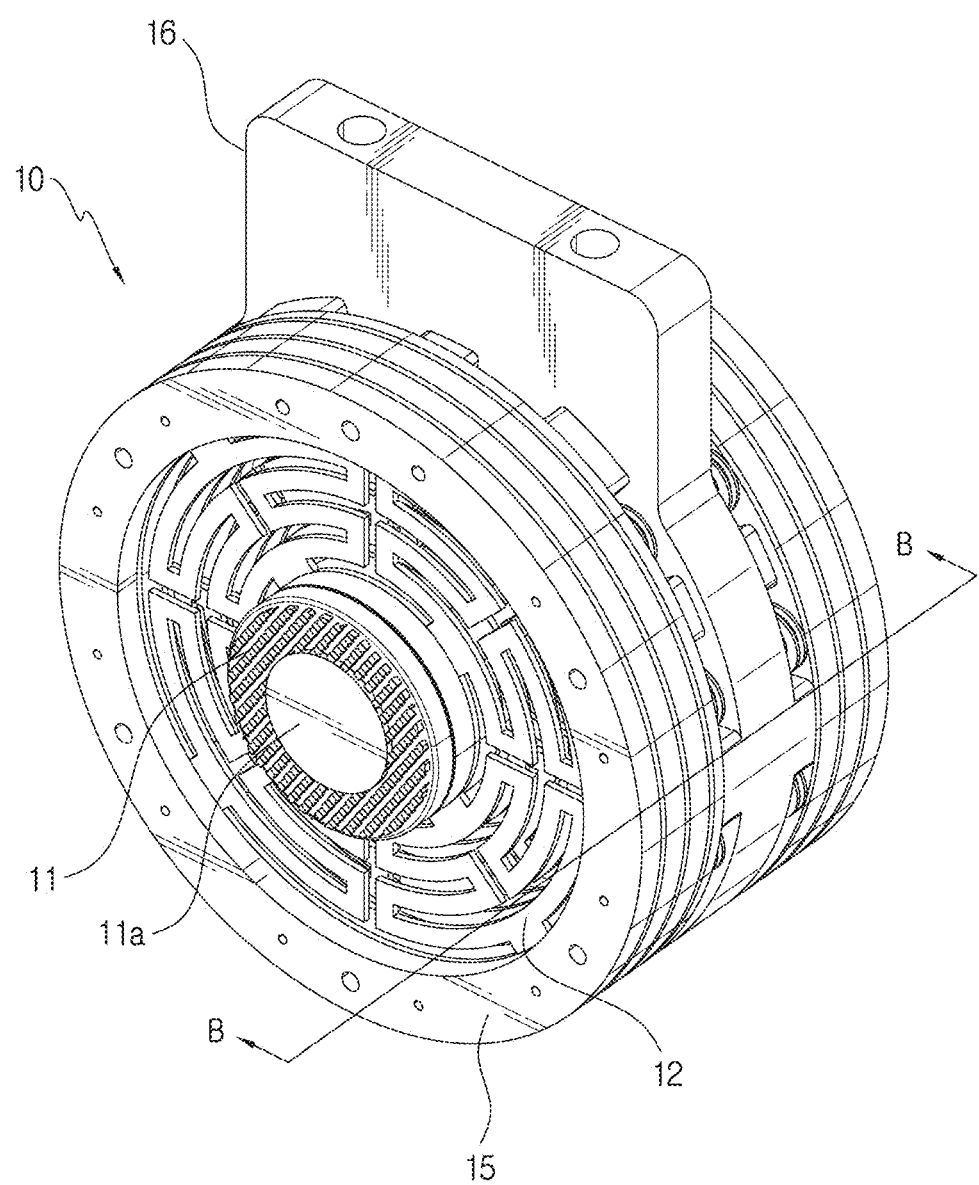
FIG. 2A is a perspective view showing a master member.
Figure 2B:
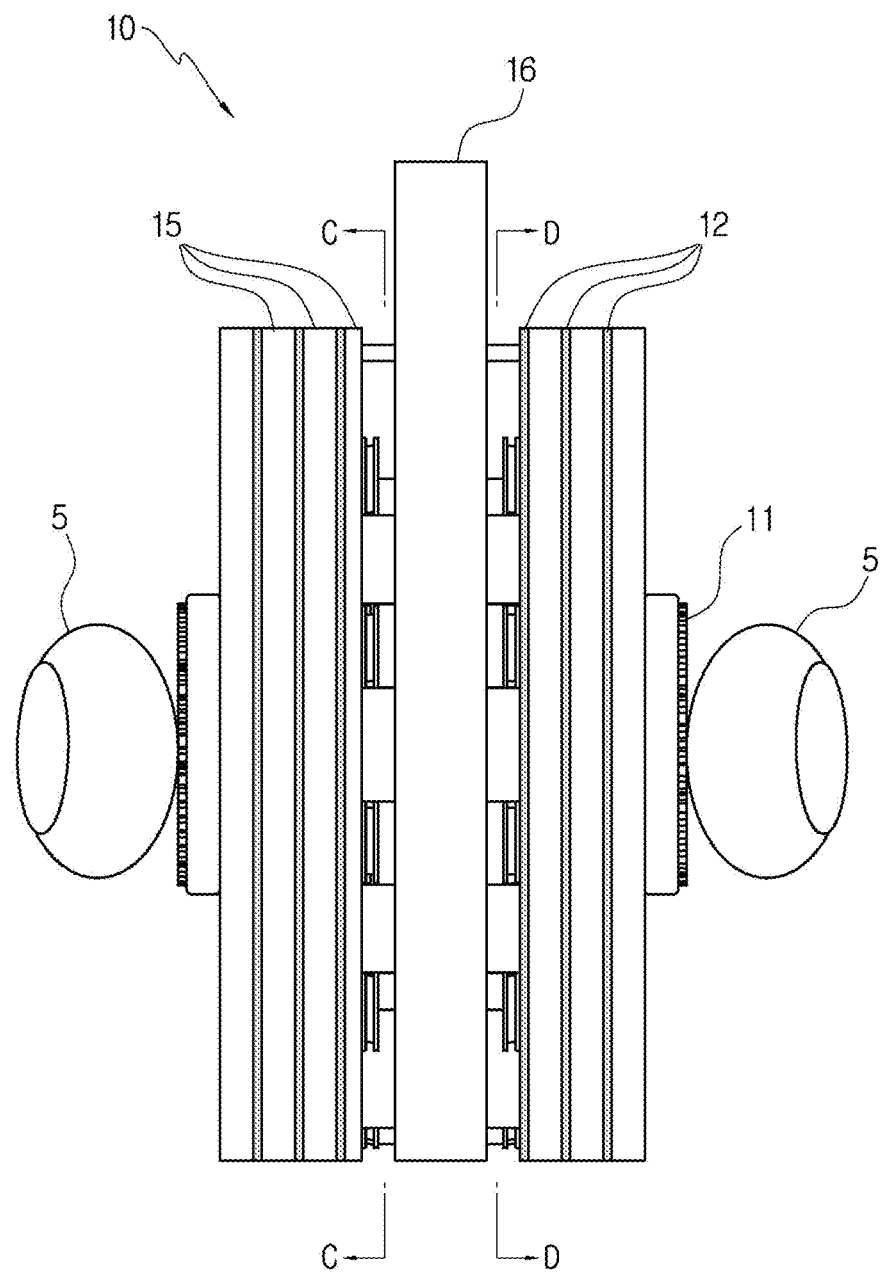
FIG. 2B is a cross-sectional view showing section B-B' in FIG. 2A.
Figure 2C:
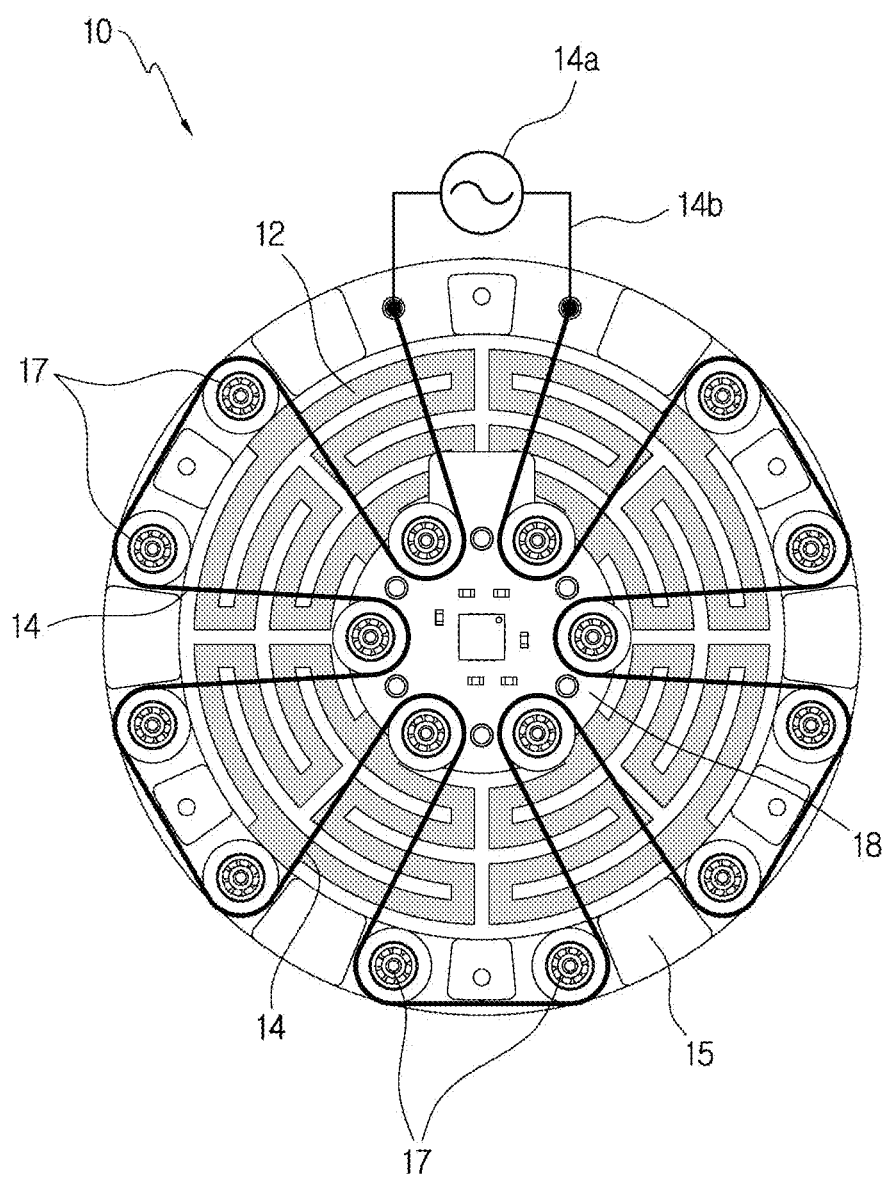
FIG. 2C is a cross-sectional view showing section C-C' in FIG. 2B.
Figure 2D:
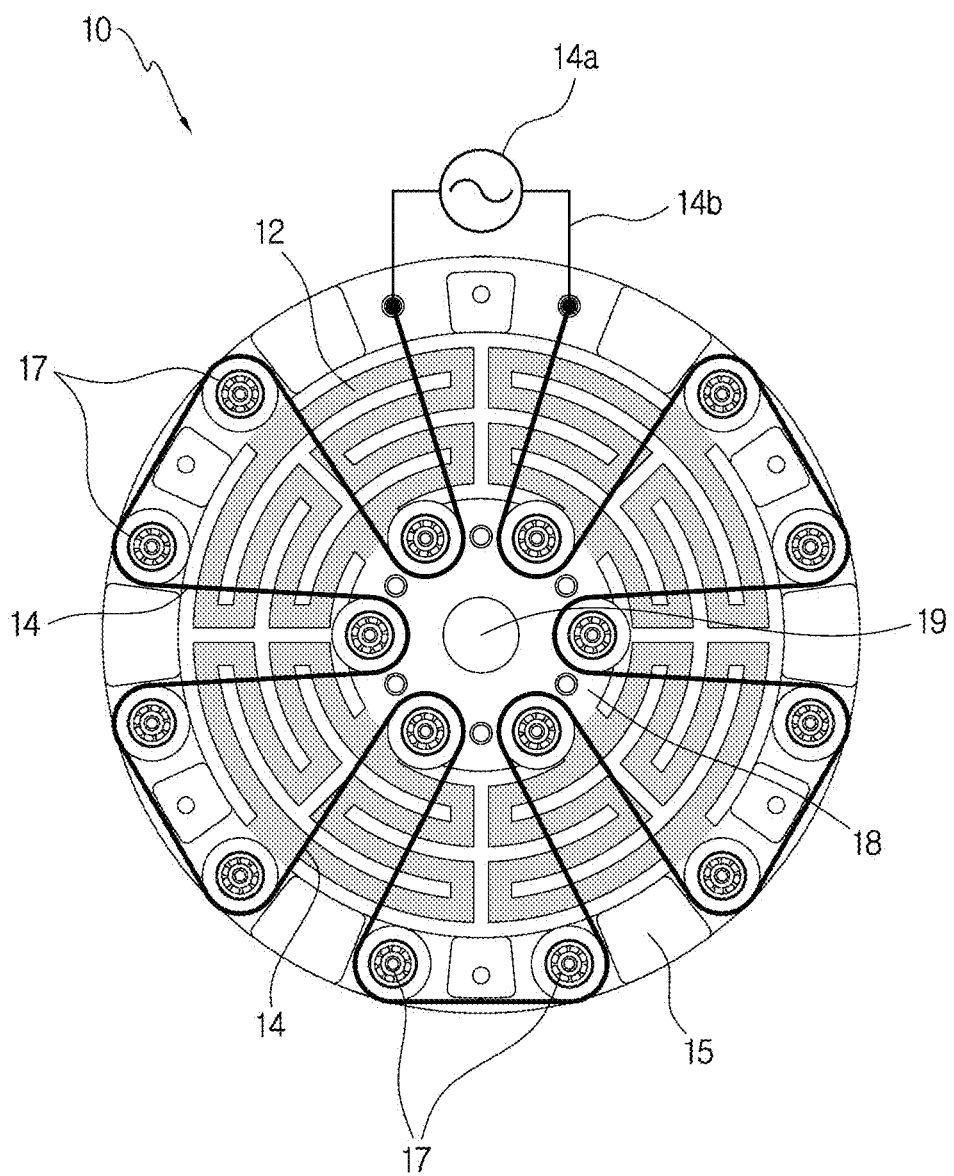
FIG. 2D is a cross-sectional view showing section D-D' in FIG. 2B.
Figure 3A:
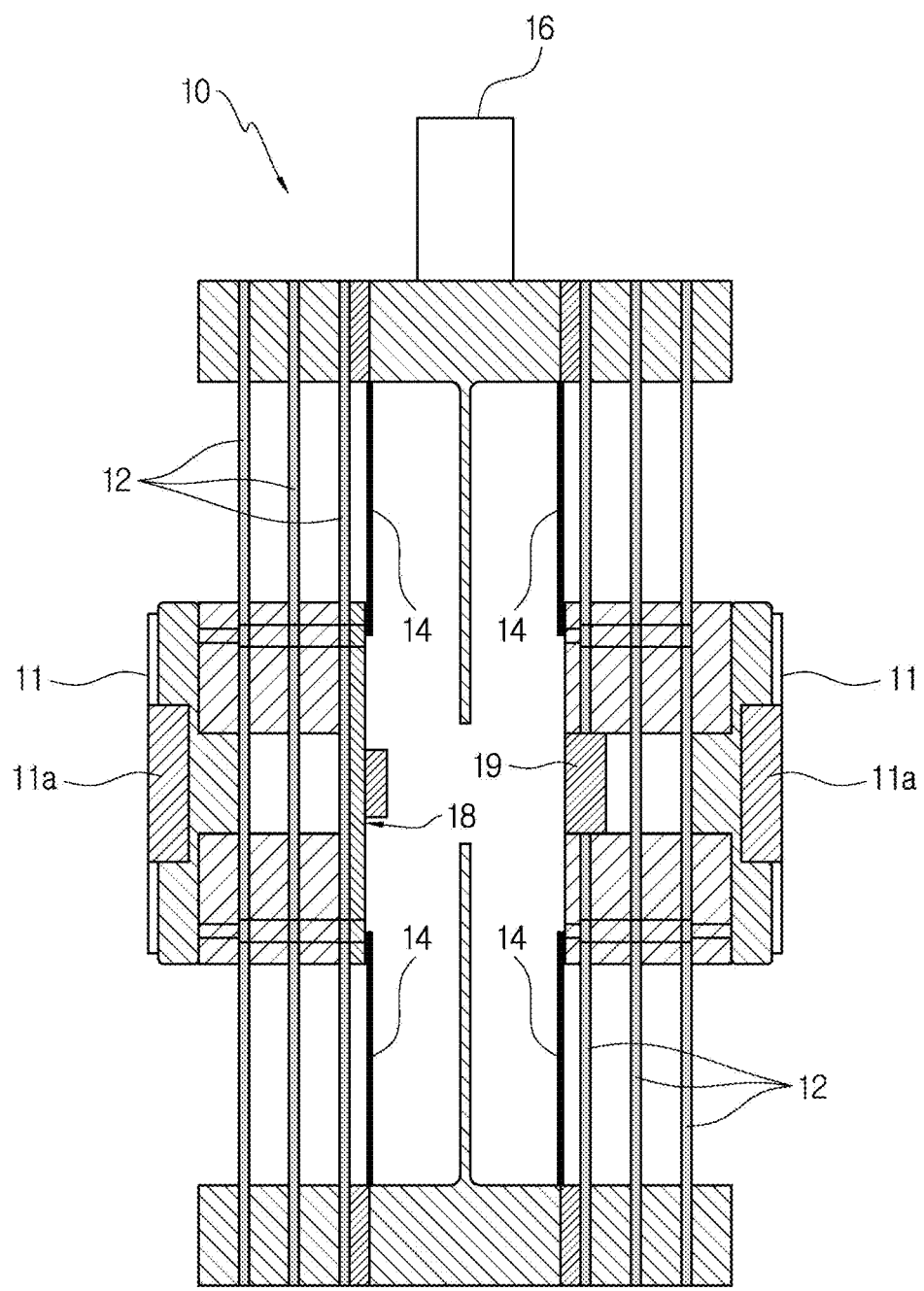
FIG. 3A is a longitudinal cross-sectional view showing a master member in a non-deformed condition of a deformable membrane.
Figure 3B:
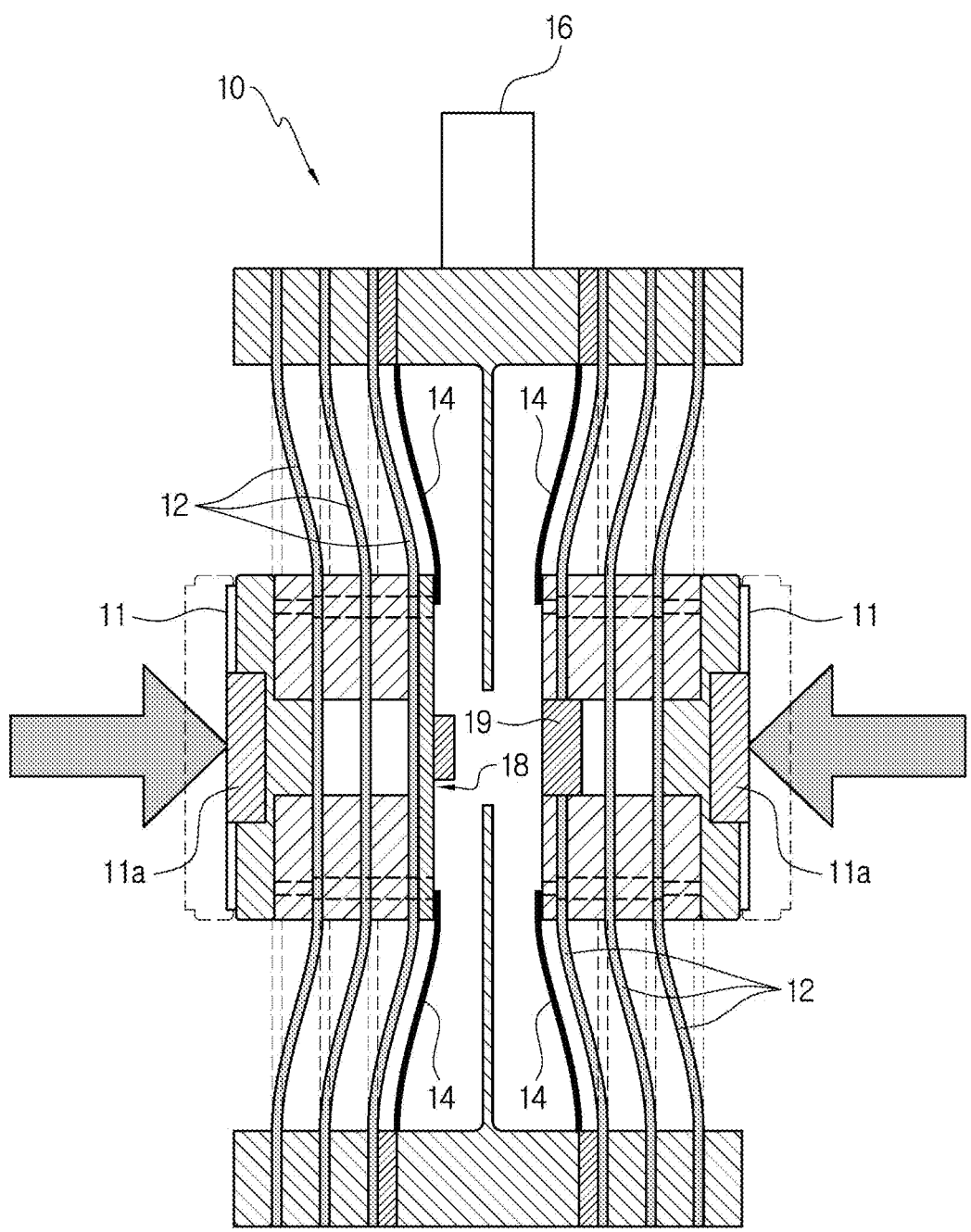
FIG. 3B is a longitudinal cross-sectional view showing a master member in a deformed condition of a deformable membrane.

FIG. 1 is a perspective view showing a tele-operated forceps-driver variable stiffness master device 100 of the present disclosure, and FIG. 2A is a perspective view showing a master member 10. Additionally, FIG. 2B is a cross-sectional view showing section B-B' in FIG. 2A, FIG. 2C is a cross-sectional view showing section C-C' in FIG. 2B, and FIG. 2D is a cross-sectional view showing section D-D' in FIG. 2B. Meanwhile, FIG. 3A is a longitudinal cross-sectional view showing the master member 10 in a non-deformed condition of a deformable membrane 12, and FIG. 3B is a longitudinal cross-sectional view showing the master member 10 in a deformed condition of the deformable membrane 12.

Hereinafter, the tele-operated forceps-driver variable stiffness master device 100 of the present disclosure and the master member 10 will be described with reference to FIGS. 1 to 3B.

The tele-operated forceps-driver variable stiffness master device 100 of the present disclosure includes the master member 10 and a slave member 20.

The master member 10 generates an input displacement signal generated by the pressing with a user's finger. The input displacement signal may be generated by a displacement sensor as described below.

The slave member 20 operates based on the input displacement signal, measures operation information, calculate a gripping force based on the operation information, and provides the master member 10 with a stiffness change command signal or force feedback based on the calculated gripping force. The slave member 20 will be described in more detail below.

The master member 10 may include a button 11, the deformable membrane 12 and a wire 14.

The button 11 may be pressed in one direction when the finger contacts the button 11. The button 11 may include a force sensor 11a to measure a change in stiffness of the master member 10. Referring to FIG. 2A, shown is an example in which the button 11 is formed in a circular shape and installed at the center of the deformable membrane 12.

The deformable membrane 12 may be connected to the button 11, and may extend in a direction perpendicular to said one direction, so the deformable membrane 12 may be deformed by the pressing with the finger. Referring to FIGS. 2A, 2C and 2D, shown is an example in which the deformable membrane is in the shape of a disc as a whole and bent multiple times in the inward direction from the circumference, and by this structure, the deformable membrane 12 can be deformed without damage.

Additionally, as shown in FIGS. 2A and 2B, the deformable membrane 12 may be formed with a multi-plate structure to sufficiently endure stiffness transmitted from the button 11 when pressed with the finger.

The wire 14 may be deformed in contraction when supplied with power to restore the deformable membrane 12 to the original state.

The wire 14 may be, for example, an actuator of a shape memory alloy.

Referring to FIGS. 2C and 2D, shown is an example in which a power supply 14a that supplies the wire 14 with power is connected to the wire 14 via an electrical wire 14b.

However, in the present disclosure, the connection relationship of the power supply 14a connected to the wire 14 with the electrical wire 14b is not necessarily limited thereto.

The master member 10 may further include a flange 15 and a wire fixture 17.

The flange 15 may be installed outside of the deformable membrane 12 to support the deformable membrane 12.

The flange 15 may be formed with a hollow donut shaped structure to support the outer side of the deformable membrane 12 and allow the deformable membrane 12 to be deformed inwards. Referring to FIGS. 2A and 2B, shown is an example in which a plurality of flanges 15 is provided and the deformable membrane 12 is interposed between the plurality of flanges 15.

The wire fixture 17 may be installed at each of the flange 15 and the deformable membrane 12 to fixedly install the wire 14.

The plurality of wire fixtures 17 may be arranged along the circumferential direction of the flanges 15 to allow the deformable membrane 12 to be deformed by tension adjustment of the wire 14, and may be arranged in a hexagonal shape near the center of the deformable membrane 12.

The wire 14 may be installed in the wire fixtures 17 installed at the flanges 15 and the deformable membrane 12 to be placed in tension by the deformation of the deformable membrane 12, and may deform the deformable membrane 12 when power is applied to the wire 14.

As shown in FIGS. 2C and 2D, the wire 14 may be placed in such a way that the wire 14 is held in two wire fixtures 17 installed at the flanges 15 and subsequently one wire fixture 17 disposed at the center of the deformable membrane 12, and held again in two wire fixtures 17 installed at the flanges 15 and one wire fixture 17 disposed at the center of the deformable membrane 12.

The master member 10 may have a symmetrical shape with respect to a neutral base 16. The master member 10 may further include a displacement sensor 18 and a magnet 19.

The displacement sensor 18 may be installed on one surface of the deformable membrane 12 disposed near the neutral base 16 to sense the displacement of the deformable membrane 12 and generate an input displacement signal.

Referring to FIGS. 2A and 2B, the neutral base 16 may be formed with a disc shaped structure where the deformable membrane 12 and the flanges 15 are installed.

The magnet 19 may be spaced apart from the displacement sensor 18, and installed on one surface of a different deformable membrane 12 with the neutral base interposed between.

When the button 11 is pressed, an attractive force is exerted between the displacement sensor 18 and the magnet 19 by the magnetism of the magnet 19.

The master member 10 may further include the force sensor 11a installed in the button 11 to sense a force applied by the contact with the finger.

Figure 4A:
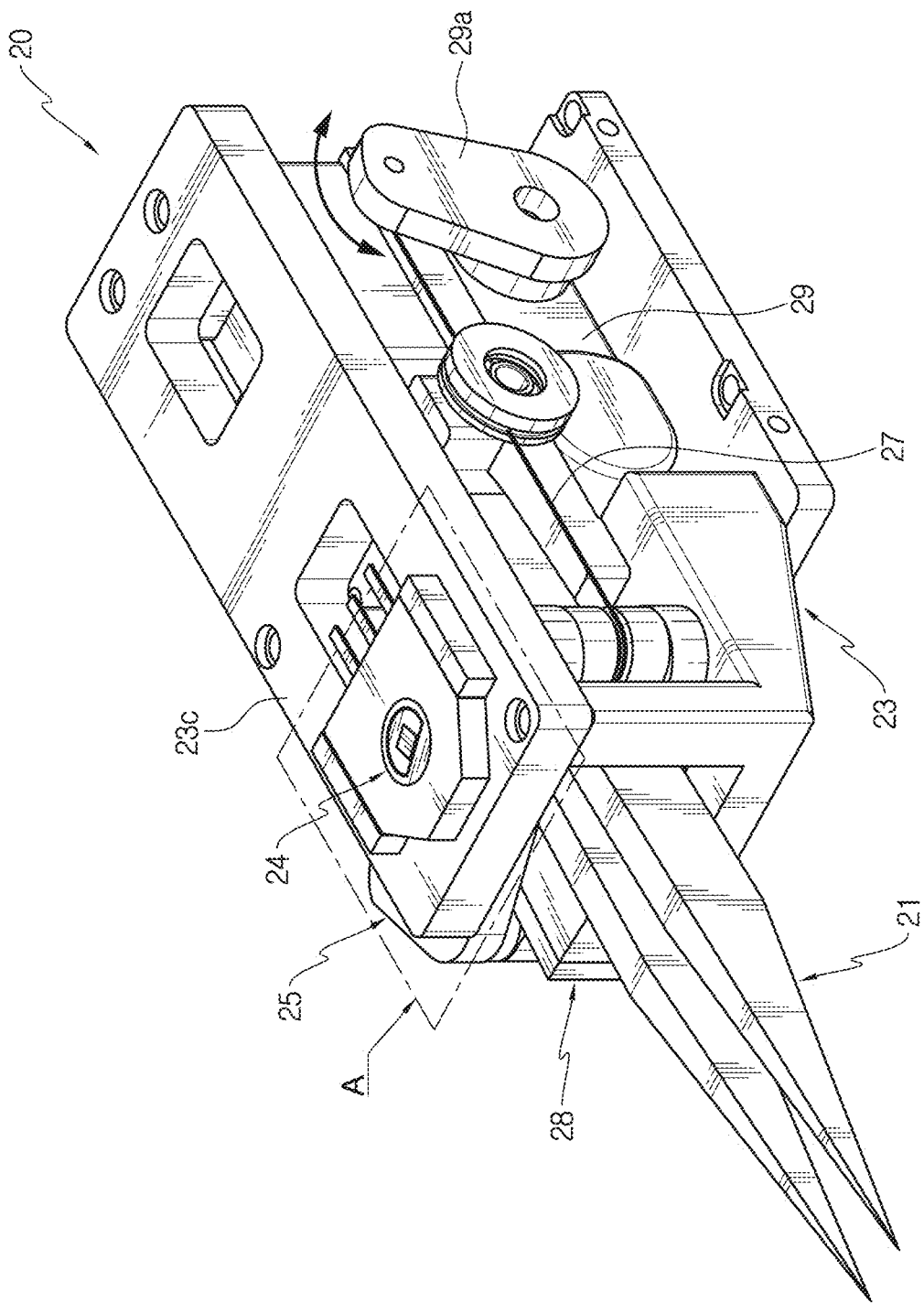
FIG. 4A is a perspective view showing a slave member.
Figure 4B:
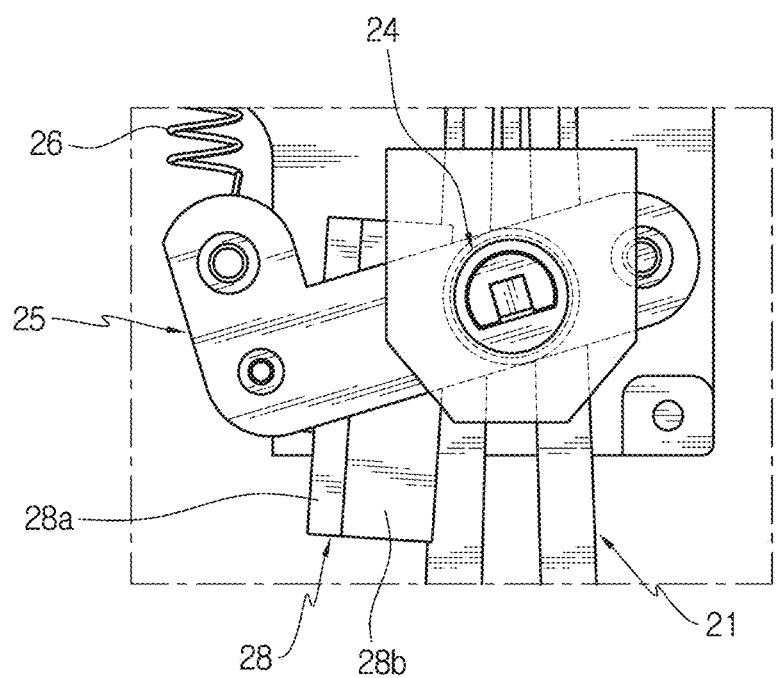
FIG. 4B is an enlarged view of section A of FIG. 4A.
Figure 4C:
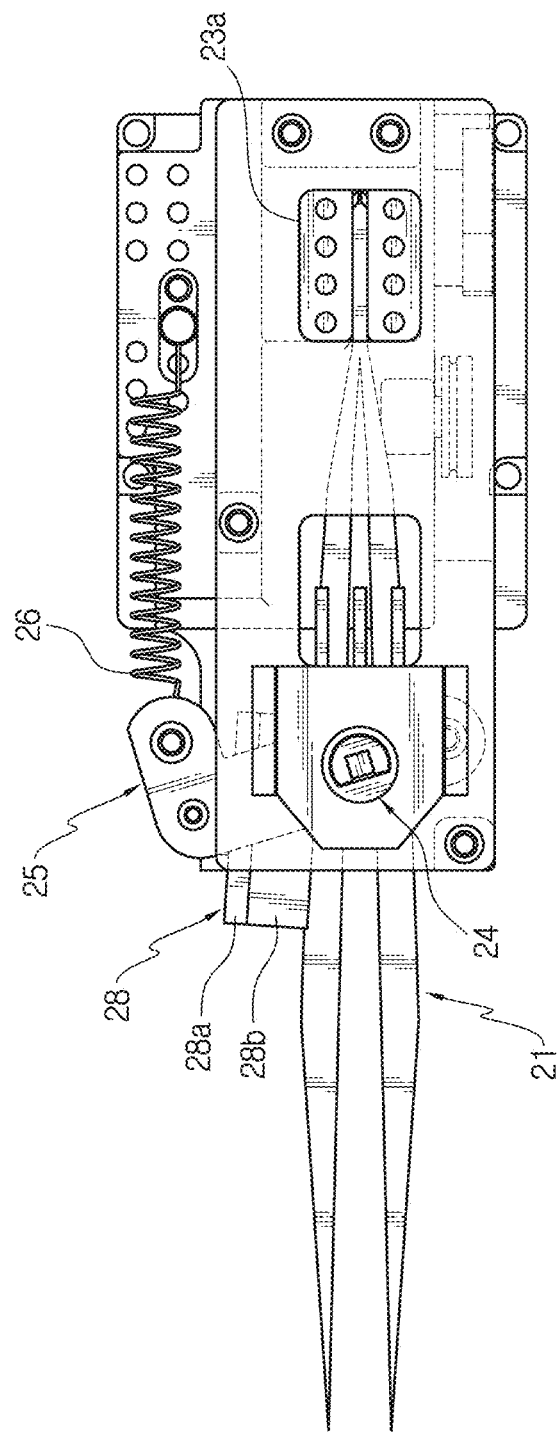
FIG. 4C is a plane view of a slave member showing an open condition of a gripper in an initial condition.
Figure 4D:
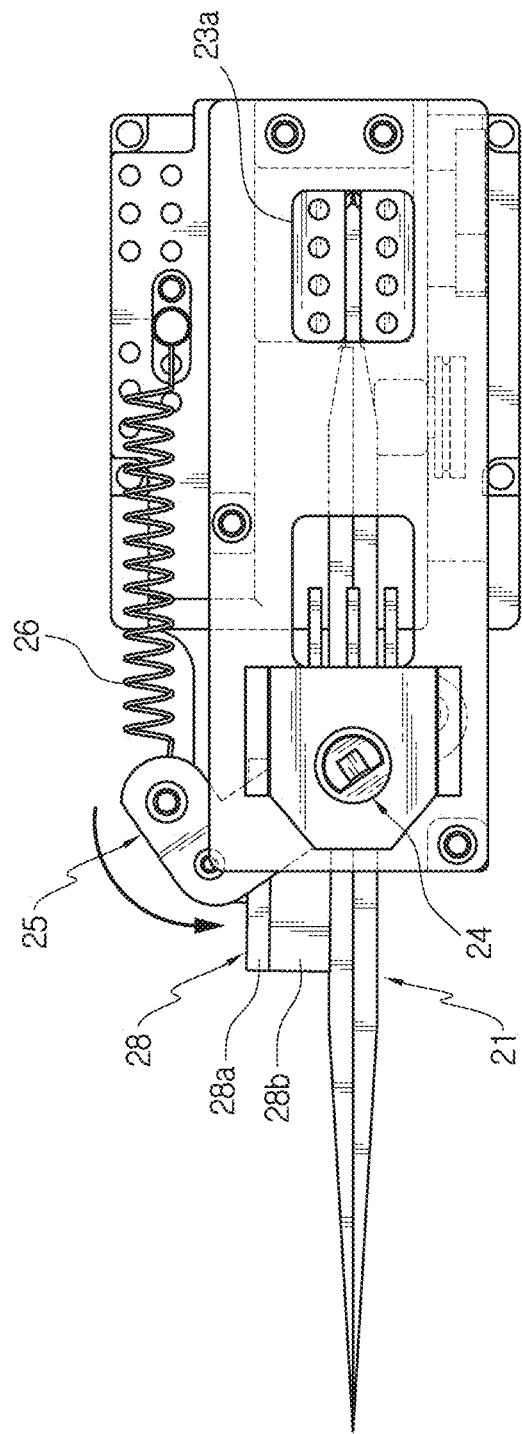
FIG. 4D is a plane view of a slave member showing a closed condition of a gripper.

FIG. 4A is a perspective view showing the slave member 20, FIG. 4B is an enlarged view of section A of FIG. 4A, and FIG. 4C is a plane view of the slave member 20 showing an open condition of a gripper 21 in an initial condition. Additionally, FIG. 4D is a plane view of the slave member 20 showing a closed condition of the gripper 21.

Referring to FIGS. 4A to 4D, the slave member 20 may include the gripper 21, a body 23, an opening and closing member 25, an elastic member 26 and a force sensing module 28.

In the present disclosure, the slave member 20 may be, for example, a forceps driver.

The gripper 21 is deformed to be open and closed. Additionally, the gripper 21 is installed in the body 23 such that the gripper 21 is received by the body 23. In the present disclosure, opening and closing of the gripper 21 may be understood as allowing one end of the gripper 21 to grasp or release the tissue or skin.

The gripper 21 may be formed with a structure in which one end is open and closed. For example, the gripper 21 may be forceps or surgical scissors, and FIG. 4A shows an example in which the gripper 21 is forceps.

The body 23 is formed to receive the gripper 21. Additionally, the body 23 may include a gripper holder 23a to couple the gripper 21. FIG. 4C and FIG. 4D shows an example in which the right end of the gripper 21 is coupled to the gripper holder 23a, and the gripper 21 is installed in the body 23 such that the gripper 21 is received in the body 23 while being open and closed.

The opening and closing member 25 is rotatably installed in the body 23 to press or release two sides of the gripper 21.

FIGS. 4A and 4B show an example in which the opening and closing member 25 is rotatably installed in the body 23 such that two ends of the opening and closing member 25 press the gripper 21.

When the opening and closing member 25 presses the two sides of the gripper 21 in one direction, the end of the gripper 21 may be closed, and in the releasing condition, the opening and closing member 25 may move away from the gripper 21 in one direction, and the gripper 21 may be open.

The elastic member 26 is connected to one side of the opening and closing member 25 to provide an elastic force to the opening and closing member 25. The elastic member 26 may be, for example, a spring. FIGS. 4C and 4D show an example in which one end of the elastic member 26 is bolt-connected to the body 23, and the other end is connected to one side of the opening and closing member 25.

A steel wire 27 is connected to the other side of the opening and closing member 25 to allow the opening and closing member 25 to rotate by the driving of a motor 29.

Meanwhile, the motor 29 may be installed in the body 23 to generate a driving force. The motor 29 is supplied with power from the power supply, and provides a rotational force to a motor output member 29a connected to the motor 29. Additionally, the steel wire 27 is installed in the motor output member 29a to provide the driving force to allow the gripper 21 to grasp when pulled by the driving of the motor 29.

Additionally, a rotational displacement sensor 24 may be installed in the body 23 to measure the extent of grasp of the gripper 21 by measuring the amount of rotation of the opening and closing member 25. Referring to FIG. 4A, shown is an example in which a cover 23c is installed on the body 23 and the rotational displacement sensor 24 is installed on the cover 23c. However, the present disclosure is not necessarily limited to this structure. The rotational displacement sensor 24 may be, for example, a positiometer.

Meanwhile, the force sensing module 28 may be installed in the body 23 between the opening and closing member 25 and the gripper 21.

The force sensing module 28 may measure a gripping force during the operation of the opening and closing member 25. Referring to FIGS. 4A and 4B, the force sensing module 28 may include a Printed Circuit Board (PCB), a sensor 28a and a stress transmitter 28b.

The PCB supplies the sensor 28a with power to receive and output information associated with a force measured by the sensor 28a. The stress transmitter 28b may be made of an elastic material, for example, urethane, to transmit the force when the opening and closing member 25 presses or releases the two sides of the gripper 21 to the sensor 28a.

Figure 5:
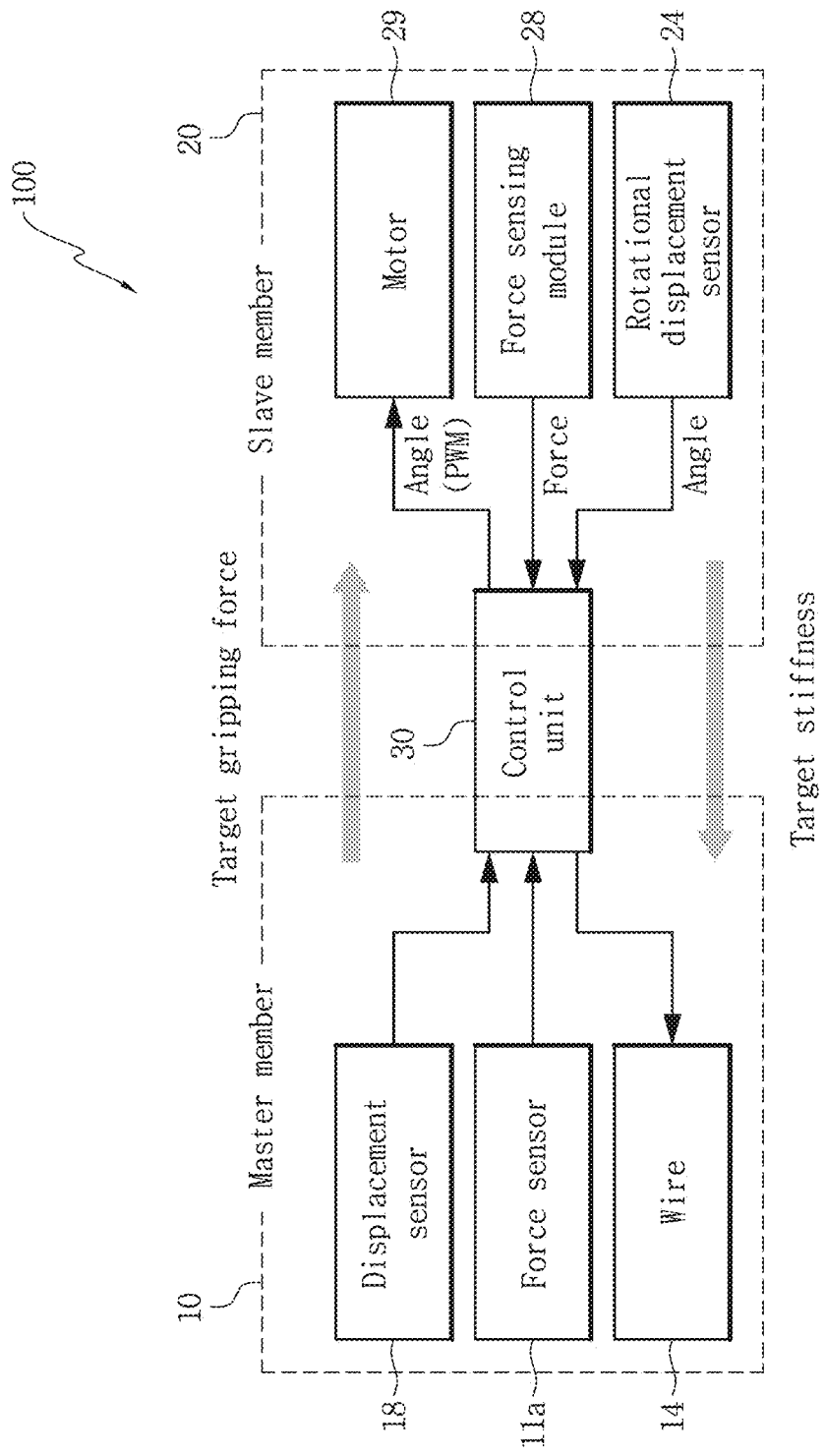
FIG. 5 is a block diagram representing the signal flow of an example of a tele-operated forceps-driver variable stiffness master device including a control unit.

FIG. 5 is a block diagram representing the signal flow of an example of the tele-operated forceps-driver variable stiffness master device 100 including a control unit 30.

Referring to FIG. 5, the tele-operated forceps-driver variable stiffness master device 100 of the present disclosure may further include the control unit 30.

The control unit 30 may receive displacement or force information from the master member 10 and control the gripping force of the slave member 20, and may receive displacement or force information from the slave member 20 and control target stiffness of the master member 10.

Additionally, the control unit 30 may receive the displacement information and the force information of the master member 10 from the displacement sensor 18 and the force sensor 11a of the master member 10 respectively, and provide an operation signal to the motor 29 of the slave member 20.

To this end, as shown in FIG. 5, the control unit 30 may be electrically connected to each of the displacement sensor 18 and the force sensor 11a of the master member 10. Additionally, the control unit 30 may be electrically connected to the motor 29 of the slave member 20.

Additionally, the control unit 30 may receive the displacement information and the force information of the slave member 20 from the rotational displacement sensor 24 and the force sensing module 28 of the slave member 20 respectively, and provide an operation signal to the wire 14 of the master member 10.

To this end, as shown in FIG. 5, the control unit 30 may be electrically connected to each of the rotational displacement sensor 24 and the force sensing module 28 of the slave member 20. Additionally, the control unit 30 may be electrically connected to the actuator of the master member 10.

Figure 6A:
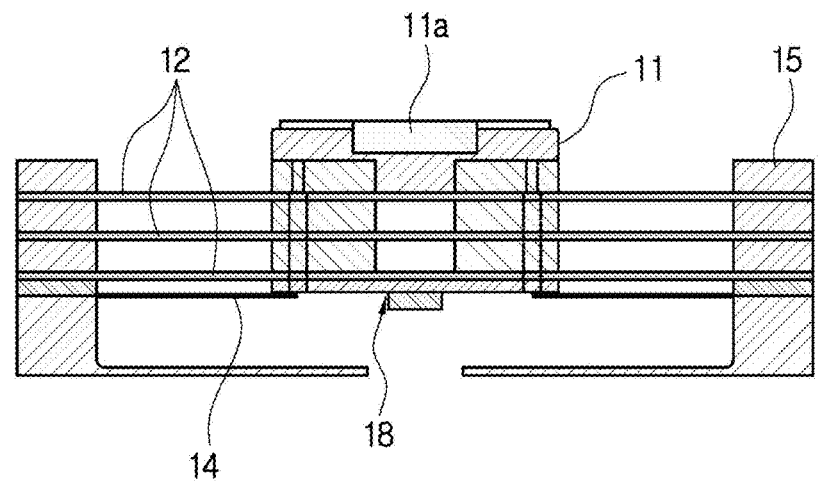
FIG. 6A is a cross-sectional view of a master member in an initial condition.
Figure 6B:
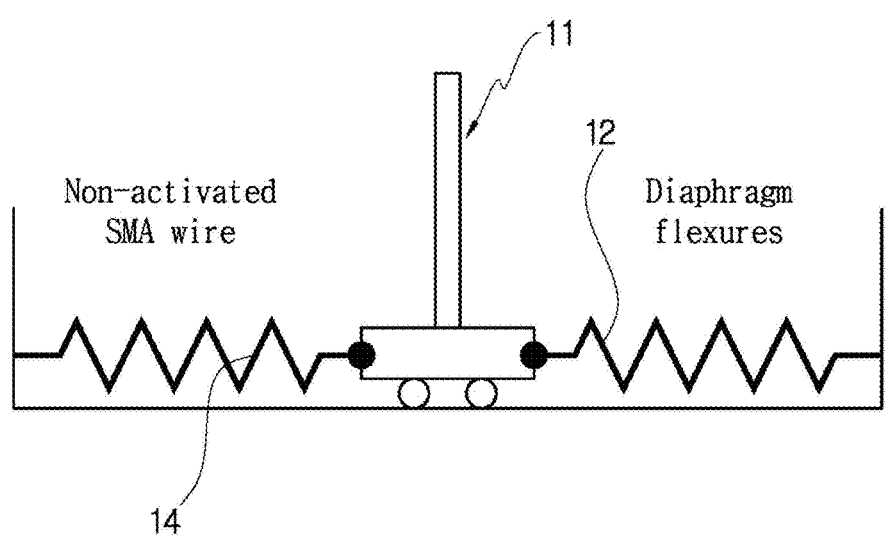
FIG. 6B is a diagram showing a wire and a deformable membrane in an initial condition.
Figure 7A:
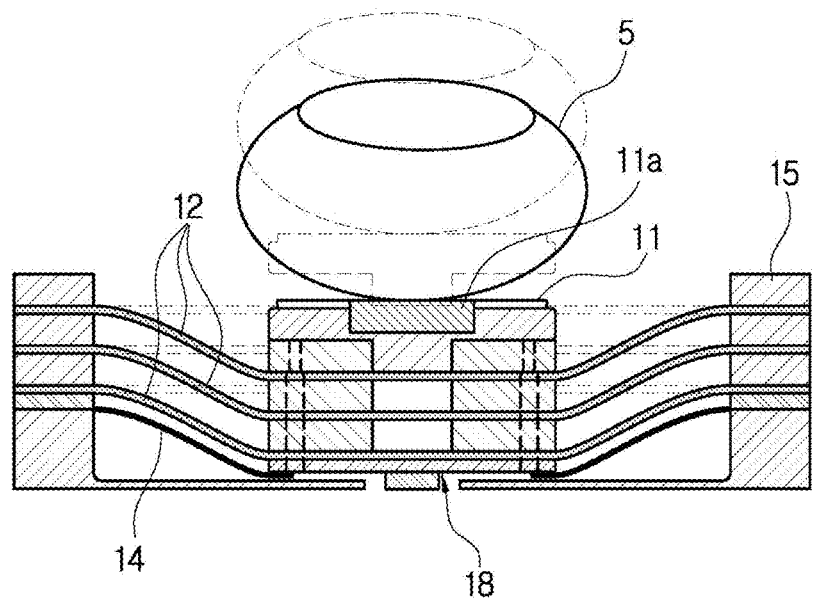
FIG. 7A is a cross-sectional view of a master member in a pressed condition of a button.
Figure 7B:
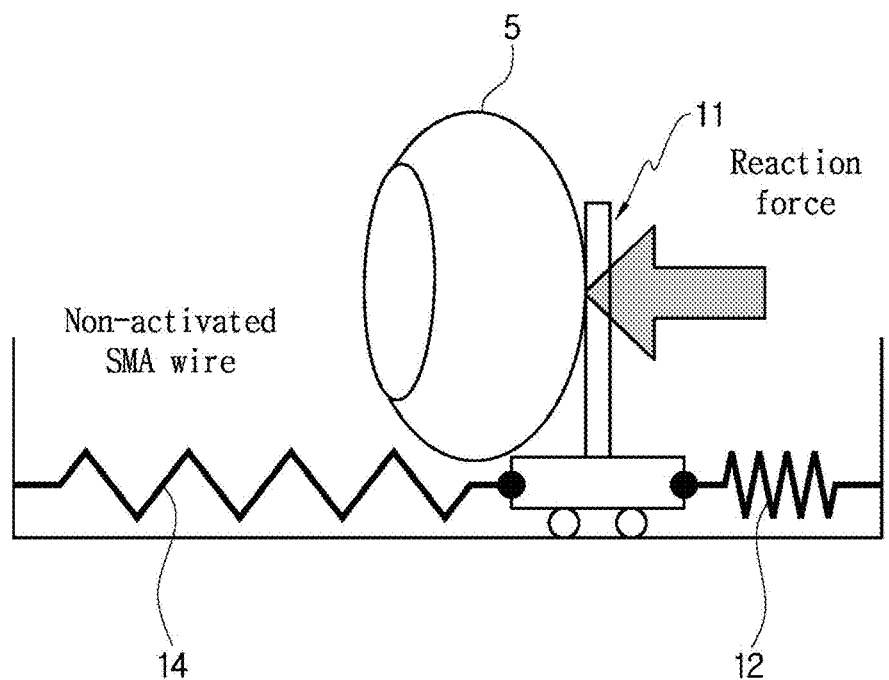
FIG. 7B is a diagram showing a wire and a deformable membrane in a pressed condition of a button.
Figure 8A:
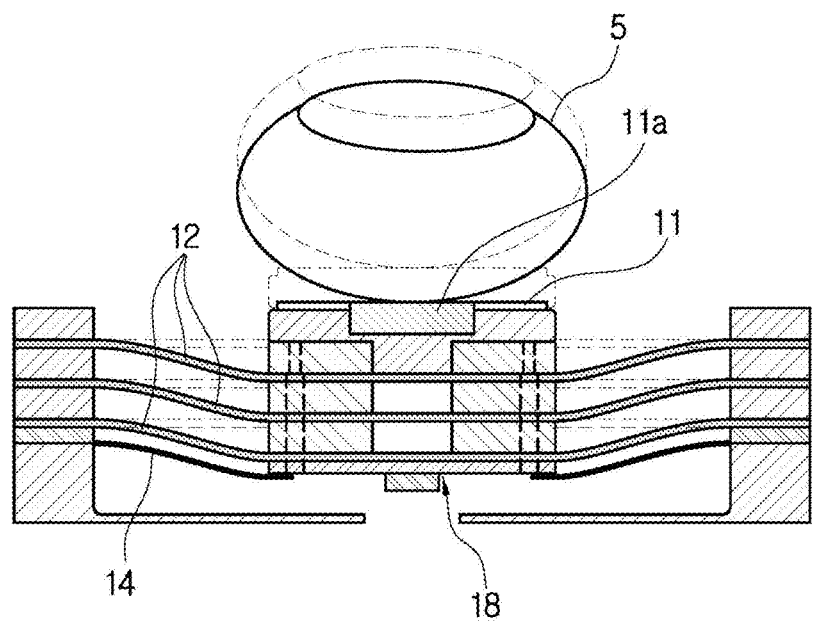
FIG. 8A is a cross-sectional view of a master member in an activated condition of a wire by haptic force feedback.
Figure 8B:
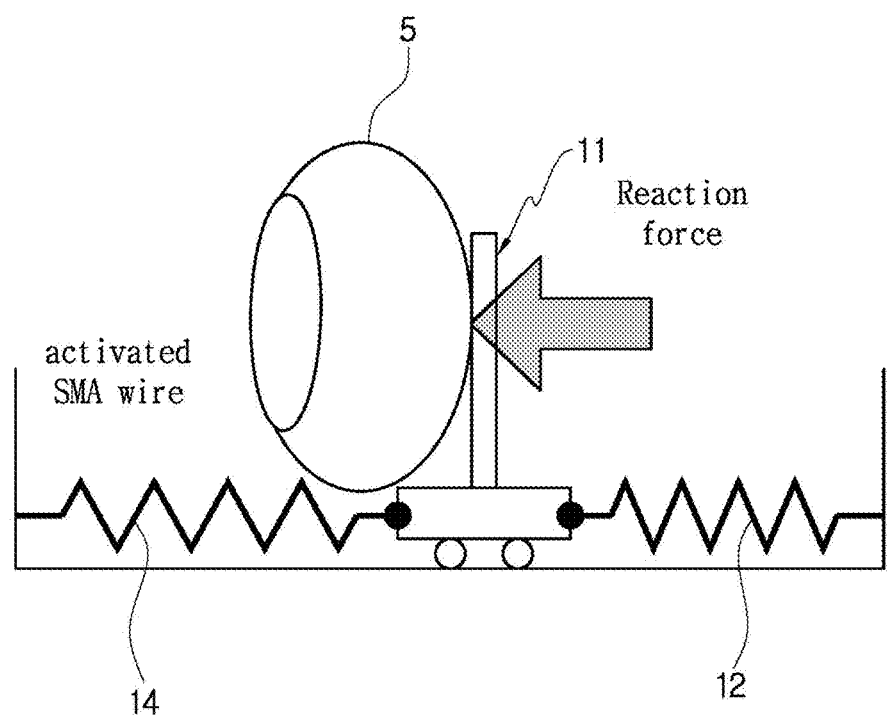
FIG. 8B is a diagram showing a wire and a deformable membrane in an activated condition of the wire by haptic force feedback.
Figure 9:
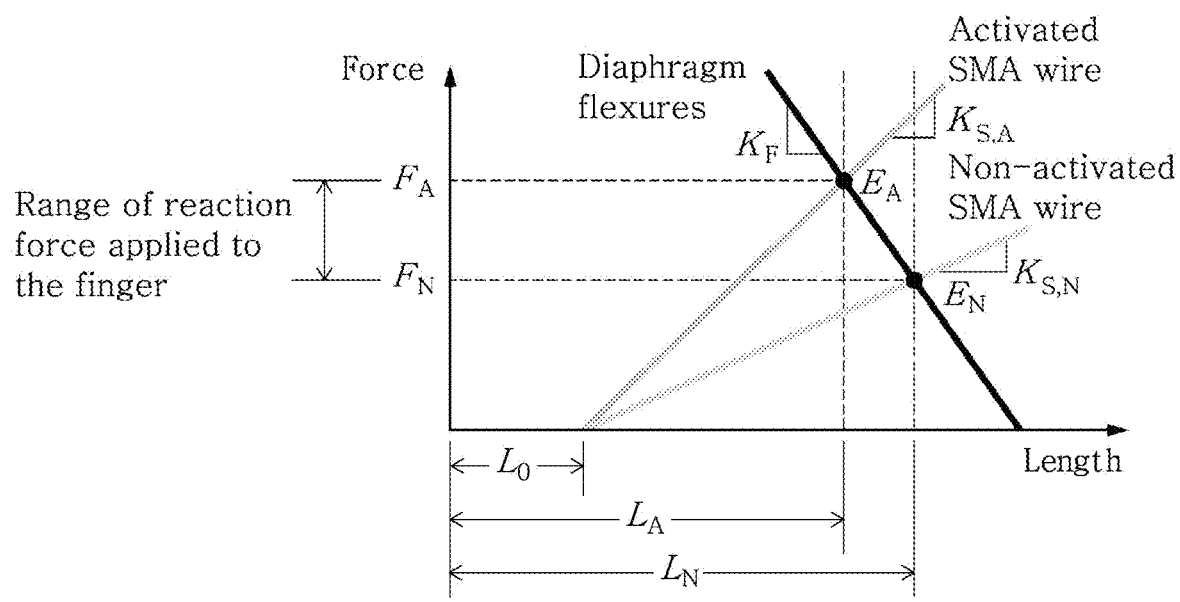
FIG. 9 is a graph showing a reaction force applied to a finger with a change in length of a wire and a deformable membrane.

FIG. 6A is a cross-sectional view of the master member 10 in the initial condition, and FIG. 6B is a diagram showing the wire 14 and the deformable membrane 12 in the initial condition. Additionally, FIG. 7A is a cross-sectional view of the master member 10 in the pressed condition of the button 11, and FIG. 7B is a diagram showing the wire 14 and the deformable membrane 12 in the pressed condition of the button 11. Meanwhile, FIG. 8A is a cross-sectional view of the master member 10 in an activated condition of the wire 14 by haptic force feedback, and FIG. 8B is a diagram showing the wire 14 and the deformable membrane 12 in the activated condition of the wire 14 by haptic force feedback. Additionally, FIG. 9 is a graph showing a reaction force applied to the finger with a change in length of the wire 14 and the deformable membrane 12.

Hereinafter, an example of manipulation of the tele-operated forceps-driver variable stiffness master device 100 of the present disclosure will be described with reference to FIGS. 6A to 9.

FIG. 6A shows a cross section of the master member 10 in the initial condition, and FIG. 6B shows an example of equilibrium between the deformable membrane 12 and the wire 14 in the initial condition. Additionally, since a load is not applied to the master member 10, the gripper 21 of the slave member 20 is open as shown in FIG. 4C.

As shown in FIG. 7A, when the finger presses the button 11 of the master member 10 in the initial condition, the deformable membrane 12 is elastically deformed, and in this instance, an elastic deformation displacement is measured by the displacement sensor 18. The control unit 30 provides a command based on the displacement measured by the displacement sensor 18 to operate the slave member 20.

In this state, as shown in FIG. 7B, the deformable membrane 12 and the wire 14 are deformed by the finger pressing the button 11 of the master member 10, producing a reaction force, but the wire 14 is still in a non-activated condition.

Meanwhile, a command based on the gripping force measured when the gripper 21 of the slave member 20 grips an object is transmitted to the master member 10.

In response to the stiffness change command, the embedded shape memory alloy wire 14 is electrically activated and stiffness of the device is changed, and a change in stiffness of the master member 10 is measured based on the values measured by the force sensor 11a and the displacement sensor 18.

Meanwhile, as shown in FIGS. 8A and 8B, the deformable membrane 12 and the wire 14 are in the deformed condition by the finger pressing the button 11 of the master member 10, and the wire 14 is activated by haptic force feedback from the slave member 20.

In addition, the bidirectional operation by the tele-operated forceps-driver variable stiffness master device 100 of the present disclosure will be described below.

The elastic deformation displacement of the deformable membrane 12 generated by pressing the button 11 of the master member 10 with the user's finger is measured by the displacement sensor 18 and the magnet 19 provided in the master member 10.

The motor 29 of the slave member 20 is driven based on the displacement value measured by the master member 10, and a rotational displacement of a rotator by the driving of the motor 29 is measured by the rotational displacement sensor 24 mounted on the slave member 20.

Additionally, a force applied to the gripper 21 while the gripper 21 is closed by the opening and closing member is measured by the force sensing module mounted in the opening and closing member.

For example, when the gripper 21 is closed to grip an object, a gripping force applied to the object is calculated based on the value measured by the force sensing module 28.

A stiffness change command is applied to the master member 10 based on the calculated gripping force.

When the stiffness change command is applied to the master member 10, the shape memory alloy of the master member 10 is electrically activated to cause a stiffness change.

A change in stiffness of the master member 10 is calculated based on the values measured by the displacement sensor 18 and the magnet 19 provided in the master member 10, and the force sensor 11a embedded in the button 11.

The tele-operated forceps-driver variable stiffness master device of the present disclosure is a system including a slave member to drive a commercially available surgical forceps mounted therein, and a master member to drive the device, and achieves fine force control and gripping force feedback, allowing a wide range of applications in the field of robot-assisted tele-operation microsurgery.

Additionally, the tele-operated forceps-driver variable stiffness master device of the present disclosure can be used in tele-operation microsurgery environment augmented reality applications by virtue of a force-blocking function of preventing the application of an excessive force to the flexible microtissue and a haptic feedback scaling function of amplifying a microgripping force and providing to a remote surgeon.

The tele-operated forceps-driver variable stiffness master device 100 as described hereinabove is not limited to the configuration and method of the embodiments described above, and some or all the embodiments may be selectively combined to make various modification.

It is obvious to those skilled in the art that the present disclosure may be embodied in other particular forms without departing from the spirit and essential features of the present disclosure. Therefore, the above detailed description should not be interpreted as being limiting in all aspects and should be considered as being exemplary. The scope of the present disclosure should be determined by the reasonable interpretation of the appended claims, and the scope of the present disclosure encompasses all modifications within the equivalent scope of the present disclosure.

What is claimed is:

1. A tele-operated forceps-driver variable stiffness master device, comprising:
   a master member to generate an input displacement signal generated by pressing with a user's finger; and
   a slave member to operate based on the input displacement signal, measure operation information, calculate a gripping force based on the operation information, and provide the master member with at least one of a stiffness change command signal or a force feedback based on the calculated gripping force;
   wherein the master member includes:
   a button that is pressed in one direction when the finger contacts the button;
   a deformable membrane connected to the button and extending in a direction perpendicular to the one direction so that the deformable membrane is deformed by the pressing of the finger;
   a wire that is deformed in contraction when supplied with power to restore the deformable membrane to an original state;
   a flange installed outside of the deformable membrane to support the deformable membrane; and
   a plurality of wire fixtures installed at each of the flange and the deformable membrane to fixedly install the wire; and
   wherein the master member is symmetric with respect to a neutral base, and
   the master member further includes:
   a displacement sensor installed on one surface of the deformable membrane disposed near the neutral base to sense displacement of the deformable membrane and generate the input displacement signal; and
   a magnet that is spaced apart from the displacement sensor and installed on one surface of a different deformable membrane with the neutral base interposed between.

2. The tele-operated forceps-driver variable stiffness master device according to claim 1, wherein the master member further includes a force sensor installed in the button to sense a force applied by the contact with the finger.

3. The tele-operated forceps-driver variable stiffness master device according to claim 1, wherein in an initial condition, when the button is pressed, the deformable membrane is elastically deformed, displacement of the deformable membrane is measured by the displacement sensor, and the slave member operates by the displacement of the deformable membrane.

4. The tele-operated forceps-driver variable stiffness master device according to claim 1, further comprising:
   a control unit to receive displacement or force information from the master member and control the gripping force of the slave member, and receive displacement or force information from the slave member and control target stiffness of the master member.

5. The tele-operated forceps-driver variable stiffness master device according to claim 1, wherein the slave member includes:
   a gripper that is deformed to be open and closed;
   a body formed to receive the gripper; and
   an opening and closing member rotatably installed in the body to press or release two sides of the gripper.

6. The tele-operated forceps-driver variable stiffness master device according to claim 5, wherein a rotational displacement sensor and a force sensing module are installed in the body, wherein the rotational displacement sensor measures an extent of grasp of the gripper by measuring an amount of rotation of the opening and closing member, and the force sensing module is interposed between the opening and closing member and the gripper to measure the gripping force during the operation of the opening and closing member.

7. The tele-operated forceps-driver variable stiffness master device according to claim 5, wherein a motor is installed in the body to generate a driving force, and a steel wire is installed between the motor and the gripper to provide the driving force to allow the gripper to grasp.

* * * * *